United States Patent [19]

Ismail

[11] Patent Number: 4,938,960
[45] Date of Patent: Jul. 3, 1990

[54] AGENTS FOR THE TREATMENT AND PROTECTION OF THE SKIN

[76] Inventor: Roshdy Ismail, Siebengebirgs-Apotheke, Siebengebirgsallee 2, 5000 Köln 41, Fed. Rep. of Germany

[21] Appl. No.: 211,125

[22] Filed: Jun. 21, 1988

Related U.S. Application Data

[63] Continuation of Ser. No. 900,727, Aug. 27, 1986, abandoned, which is a continuation-in-part of Ser. No. 706,723, Feb. 28, 1985, abandoned.

[30] Foreign Application Priority Data

| Date | Country | Number |
|---|---|---|
| Mar. 7, 1984 [DE] | Fed. Rep. of Germany | 3408258 |
| Mar. 23, 1984 [DE] | Fed. Rep. of Germany | 3410641 |
| Jun. 1, 1984 [DE] | Fed. Rep. of Germany | 3420459 |
| Jul. 25, 1984 [DE] | Fed. Rep. of Germany | 3427374 |
| Sep. 25, 1984 [DE] | Fed. Rep. of Germany | 3435098 |
| Nov. 15, 1984 [DE] | Fed. Rep. of Germany | 3441711 |
| Feb. 12, 1985 [DE] | Fed. Rep. of Germany | 3504695 |

[51] Int. Cl.$^5$ .................... A61K 35/78; A61K 31/355
[52] U.S. Cl. ................... 424/195.1; 514/356; 514/458; 514/548; 514/887
[58] Field of Search ............ 426/195.1; 514/356, 514/458, 548, 887

[56] References Cited

U.S. PATENT DOCUMENTS

| | | | |
|---|---|---|---|
| 4,144,325 | 3/1974 | Voyt | 514/458 X |
| 4,454,159 | 6/1984 | Musher | 514/458 X |
| 4,525,344 | 6/1985 | Totsky | 514/458 X |

FOREIGN PATENT DOCUMENTS 964444  7/1964  United Kingdom .

OTHER PUBLICATIONS

Machlin–"Vitamin E, A Comprehensive Treatise", (Textbook), Pub. Maruel Dekker, Inc.; pp. 579–858 & 597 (1980).

*Primary Examiner*—Leonard Schenkman
*Attorney, Agent, or Firm*—Wegner & Bretschneider

[57] ABSTRACT

The present invention relates to a method for the treatment and protection of human and animal skin which contains vitamin E in a high dose and, in addition, may optionally further contain vitamin C, vitamin A, vitamins of the B series, blood circulation-promoting agents and/or vasodilators, phospholipids, unsaturated fatty acids and/or emulsifiers.

49 Claims, No Drawings

AGENTS FOR THE TREATMENT AND PROTECTION OF THE SKIN

CROSS-REFERENCE TO RELATED APPLICATION

This application is a continuation of U.S. application Ser. No. 900,727, filed Aug. 27, 1986 which is a continuation-in-part of Ser. No. 706,723 filed Feb. 28, 1985 now abandoned.

BACKGROUND OF THE INVENTION

The present invention relates to an agent containing vitamin E for treating and protecting the skin.

Vitamin E is known as an antioxidant and protective vitamin for phospholipids of the cell membrane. It maintains the permeability and stability of the cell membrane; cf. Lucy, Annals N.Y. Academy of Science 203, p. 4 (1972). There has further been known that vitamin E has a membrane-sealing effect; cf. F. Mittelbach and G. Bodechtel, Munchner Medizinische Wochenschrift 110 (1968) 36: pp. 1988–1993. In erythrocytes, the simplest cells of the human body, there has been found that vitamin E provides a protective effect for the cell membrane. In tests with animals and humans it has been proven that anemia is a first signal of a deficiency of vitamin E. The hemolysis of the erythrocytes will normalize upon administration of high doses of vitamin E; cf. William J. Darbey Vitamin Horm., 26 (50) pp. 685–704 (1968) and Phelps DL Pediatrics 63 (6) pp. 933–935 (1979). From these references from the literature, there it is apparent that after the oral administration of from 200 to 800 mg of vitamin E over a period of from 1 to 4 days the hemolysis of the erythrocytes is significantly improved as compared to patients suffering from vitamin E deficiency.

Vitamin E has further been used to treat sickle cell anemia over a period of from 6 to 35 weeks; cf. Natt CL. Am. J. Clin. 33, pp. 968–971 (1980); Natt CL. Am. J. Clin. Nutr. 32, pp. 1359–1362 (1979); Gawlik G. M. Fed. Proc. 35 (3), p. 252 (1976) and Gorash L. Bieri J. G. et al. Univ. Conn. Farmington, GT.

It has further been known that a daily dose of 750 mg of vitamin E over a period of from 3 to 6 months was successfully used to treat thalassemia patients, whereupon a normalization of the hemolysis of the erythrocytes was observed; cf. Kahane I. ISR. J. Med. 12 (1), pp. 11–15 (1976).

Vitamin E has further been successfully applied to patients suffering from an acute hepatitis or an alcoholic hepatitis who have a deficiency in vitamin E in serum; cf. Yoshiakawa T., Takemura S., Kato H. et al., Japan. J. Gastrovent, 74/7, pp. 732–739 (1977). Eventually, vitamin E has been used to treat patients suffering from anemia due to an iron deficiency, in which such treatment has caused an improvement or normalization of the lipid metabolism in the bone marrow occuring in the course of from 4 to 8 weeks; cf. Takoshi Itaga, Central Clinical Laboratory Nagasaki University of Medicine, Japan.

In the German Patent Application Nos. P 34 20 738, P 34 05 928, P 34 05 239, P 34 07 025, P 34 08 260, P 34 16 162, P 34 32 881, P 34 05 240, P 34 02 930, P 34 07 024, P 34 07 026, P 34 15 250, P 34 27 193 the use of vitamin E has further been proposed for the treatment of the veins, of the anal region and of rheumatic diseases.

It has further been known that cholesterol in human and animal skin is converted by ultraviolet radiation into cholesterol-alpha-oxide, a substance known to be carcinogenic Experiments with mice have shown that upon administration of vitamins E and C and of two further antioxidants no cholesterol-alpha-oxide will be formed (Pharm. Indu. 36, Nr. 3 (1974) Anschel, U.S.A.).

It has now surprisingly been found that vitamin E and combinations comprising vitamin E together with other active substances, more specifically, are suitable as agents for the treatment of eczema, skin tetter, skin inflammations itch, allergies, wrinkles, and wounds. Moreover, the agents according to the invention can be employed as protective agents against ultraviolet light. The agents according to the invention are further suitable as skin-protecting agents in cases of exposure to radiation, e.g. of cancer patients. This new range of indications was not foreseeable from the state of the art and will open a new wide field of applications for vitamin E. The use of vitamin E, at long sight, will result in a stabilization and permanent elimination of the symptoms, so that the probability of a relapse is very low. However, the combined preparations containing vitamin E will have to be taken over an extended period of time, for about 6 months or longer.

SUMMARY OF THE INVENTION

Thus, it is the object of the present invention to provide agents containing vitamin E for use in the treatment and the protection of human and animal skin, which agents are characterized such that it contains a high dose of vitamin E as the essential ingredient, in addition to conventional carriers and/or excipients and, optionally, vitamin C, vitamin A, vitamins of the B series, blood circulation promoters and/or other vasodilators, phospholipids, and unsaturated fatty acids and/or emulsifiers.

DETAILED DESCRIPTION OF THE INVENTION

Since vitamin E is liquid at room temperature, the capsule offers itself as a form of application in the first place. The other active ingredients are incorporated in vitamin E and, if desired, in a readily liquid neutral oil and a solutizer, and introduced into the capsules in a per se known manner. Here, emulsifiers such as Tween, may be used.

In the agents according to the invention, above all, a sufficient dosage of vitamin E which should be at least 200 mg is crucial for the efficacy of vitamin E. Lower dosages of vitamin E are useless, since large parts thereof are destroyed by the gastric acid and thereby lose their activity; cf. Arthur Vogelsang, Angiology, 21, pp. 275–279 (1970).

If, in the past, sometimes low amounts of vitamin E, viz. up to 40 mg, have been employed in combination preparations, these amounts with certainty were ineffective due to the low doses. For the treatment, the dosage should be in the range of from 200 to 1,000 mg. Preferably dosage forms containing from 250 to 600 mg of vitamin E are used. Typical combination preparations contain from 300 to 500 mg of vitamin E per dosage unit.

Vitamin E may be employed in all of its alpha-forms, as the free tocopherol as well as its ester of natural origin or of synthetic origin. Said ester can be the acetate, succinate or any other suitable ester. For an ointment, gel or cream, respectively, the free tocopherol, such as D,L-alpha-tocopherol or D-alpha-tocopherol, is preferred to be used.

Surprisingly, the action of vitamin E is significantly increased in the presence of vasodilators and/or blood circulation-promoting agents by synergism, and, thus, the duration of treatment is shortened.

Also unexpectedly, the absorption of vitamin E through the skin is also particularly increased by the presence of agents promoting blood circulation such as heparin sodium, *Extract. Hippocastani* etc. When heparin sodium is used, the high dose of from 30,000 to 150,000 I.U. is preferred.

Further agents which will essentially increase the action of vitamin E and, hence, can be used for the present invention are agents promoting the blood circulation such as B-Hydroxyethylrut oside, trimethylrutoside, *Extract. Arnicae* nicotinic acid, nicotinic acid ester and derivatives thereof, xanthinol nicotinate, inositol niootinate, and salicylic acid or the esters thereof, dihydroergotoxine methanesulfonate, dihydroergocornine methanesulphonate, dihydroergocristine methanesulphonate, B-hydroxyethylsalicylate 01. *juniperi* 01. *pini pumilionis* (dwarf pine oil), 01. *eucalypti* 01. *rosmarinae Tinot. camphorae* (or camphor, respectively), Cinnarizine, Vincamine, Pentoxfiylline, Bamethan sulfate, Bencyclan hydrogenfumarate, beta-pyridylcarbinol, Ginkgo flavoglycosides. Further derivatives of the agents promoting blood circulation and vasodilators may also be used.

As vegetable vasodilators there ought to be mentioned, e.g., *Extract. calendulae* from *Herba calendulae*. The agents promoting blood circulation may also be used in their retard forms (sustained release drugs). Numerous blood circulation-promoters, such as B-hydroxyethylrutoside, also have anticoagulant properties.

The combinations comprising sufficient amounts according to the invention further improve the blood circulation in the extremities, the eye periphery, the inner ear and the cerebrum. If dimethylaminoethanol or its derivatives or salts, respectively, will further be added to the combinations according to the invention, the blood flow in the brain, in the central nervous system and the concentrating ability are enhanced.

The combinations according to the invention further have advantageous effects on the lipid and cholesterol metabolisms.

The agents according to the invention may also be externally applied in the form of a cream, gel, ointment or lotion or a solution, optionally together with emulsifier(s). In this case the concentration of vitamin E is from 0.5% to 20% by weight. Amounts of from 4% to 10% by weight are particularly preferred. Other administration forms may also be prepared, e.g. spray, tincture or an alcoholic solution. Isopropanol or propane diol are particularly preferred solvents which, at the same time, promote blood circulation as well. In this case, the concentration of vitamin E may amount up to 32% by weight. A concentration of up to 25% by weight per administration form is preferred.

As the conventional bases for ointments or creams, *Eucerin cum aqua, Ungentum Cordes* or *Ungentum emulsificans,* may be used as well as other water-insoluble ointment bases and mixtures thereof. For example, suitable ointment bases are wool wax, petrolatum DAB 8, highly fluid paraffin and mixtures thereof. They may also contain emulsifiers such as cetylstearylalcohol.

Also suitable as bases for ointments are *Unguentum alcoholum lanae aquosum* containing Cetiol (oleyl oleate) and *Unguentum lanette,* cetylstearylalcohol, Cetiol DAB 8 and Aqua conservata.

Advantageously, further vitamins, e.g. the vitamins C, A, $B_1$, $B_2$ and $B_6$, may be added to the agents according to the invention An ointment according to the invention desirably contains the following components as the base materials: 70% to 30% by weight, preferably 60% to 40% by weight, of water, 30% to 5% by weight, preferably 25% to 7% by weight, of Cetiol (oleyl oleate), and 30% to 2% by weight, preferably 25% to 2% by weight, of cetylstearylalcohol or other aliphatic alcohols.

The cetylstearylalcohol altogether or in part may be replaced by other emulsifying alcohols, such as, e.g., aliphatic alcohols or wool wax alcohols or diols, respectively, stearinol, monoglycerides esterified with aliphatic acids or similar substances. There may also be added, e.g., paraffin or petrolatum or other suitable materials in order to render the ointment spreadable. Cetiol (oleyl oleate) may also be completely or partially replaced by other emulsifiers such as Tween 20 or Tween 80 etc. A particularly preferred combination as a base for ointments or creams containing vitamin E is as follows:

30% to 20% by weight of cetylstearylalcohol,
20% to 10% by weight of Cetiol (oleyl oleate),
60% to 40% by weight of water (aqua conservata).

It has been known that ointment bases containing water such as *Unguentum emulsificans aquosum* and *Unguentum alcoholum lanae aquosum* are suitable for processing water-soluble active substances. However, it is surprising that ointment bases containing water up to an amount of approximately more than 50% are very well suitable for processing lipophilic active substances such as vitamin E.

It has also unexpectedly been found that the agents according to the present invention are particularly beneficial if these agents additionally contain vitamin A. More specifically, the duration of the treatment will be shortened. Thus, the present invention includes those agents for the treatment and protection of the skin that contain vitamin A together with vitamin E and blood circulation-promoting agents. Vitamin A can be employed as vitamin A palmitate, vitamin A acetate, a further ester of vitamin A and/or as beta-carotene. The amount of vitamin A in the dosage unit is to be selected so that the maximum daily dose will not exceed 50,000 I.U. i.e. when two dosage units are to be administered per day, the dosage unit should contain a maximum of 25,000 I.U. The dosage of vitamin A in the agents according to the invention usually is between 5,000 and 25,000 I.U., and preferably between 6,000 and 15,000 I.U.

The vitamins A and E very strongly tend to clog in an aqueous medium, more particularly so in the presence of other active substances. Thus, it may happen that the lipophilic valuable substances are not absorbed. It has now been determined that surprisingly small amounts of about 1% of an emulsifier are sufficient to prevent clogging. The active substances are more readily dispersed or suspended, respectively, in the aqueous medium. This is advantageous in that the absorption by the intestine is facilitated. A higher amount of emulsifier is not necessary, as in most cases 1% to 7% will suffice to prevent clogging. Emulsifiers may be used in amounts up to 10% or even more, but these larger amounts have the drawback that side-effects may possibly occur when the medicament is administered over an extended period of time.

Conventional emulsifiers as used in medical preparations can be employed, such as Tween 20, Cremophor ®, aliphatic alcohols, partially esterified triglycerides etc. However, in the present invention Tween 80 and Cetiol are preferred. It has been observed that upon the addition of about 10% of emulsifier the emulsification is not substantially improved over that effected by the addition of 5% of emulsifier.

Lecithin in a concentration between 1% and 13% may also be used as emulsifier. This favors the absorption of the combination of vitamins A and E and more specifically the resorption of vitamin A. Although upon the use of large amounts of lecithin, up to 50%, a positive effect is determinable, small amounts of lecithin will suffice to prevent clogging of the lipophilic vitamins and to positively affect the optimal resorption. It is further recommended to add about 1% of a conventional emulsifier such as Tween 80, as thereby, the miscibility of lecithin with the two vitamins is positively affected and clogging is prevented. With respect to the resorption properties the use of conventional emulsifiers such as, e.g. Tween 80, in an amount of about 1% together with from 1% to 13% of lecithin is particularly beneficial. There may also be used Tween 20, Cetiol (oleyl oleate) and Cremophor ® types. As the lecithin preparation the soybean lecithin is preferred.

The agents according to the invention are also suitable as protectives against ultraviolet light. For this purpose UV stabilizers are added which are compatible with the skin and lipophilic as well as hydrophilic such as, e.g., Eusolex ®. The UV stabilizers can be added in an amount of from 0.1% to 20% by weight, and preferably of from 0.5% to 10% by weight.

Further possible additives include cod liver oil and/or unsaturated fatty acids, e.g. linoleic acid, linolenic acid or oleic acid. Instead of the unsaturated fatty acids there may also be used silicone oils or polysiloxanes.

The agents according to the invention are particularly suitable as skin-protective agents when combined with phospholipids, e.g. with lecithin. The phospholipids will accelerate the absorption of vitamin E by the skin and, thereby, increase the efficacy of the vitamin E preparations.

In order to treat skin inflammations there may further be added up to 12% by weight, based on the dosage unit, of Bufexamac to the vitamin E preparations according to the invention, 3% to 10% by weight being preferred.

It has been known that Bufexamac cream or ointment is suitable for the treatment of skin inflammations, allergies, eczema and itch. However, the duration of the treatment is surprisingly shortened in the presence of vitamin E, and the probability of a relapse to occur is reduced. After the subsidence of the disease rubbing with only a vitamin E ointment is preferred to prevent a relapse.

For the treatment of allergies the agents according to the invention may be combined with active antiallergic substances, more specifically antihistaminics. An addition of vitamin E to those allergically active materials accelerates the healing process.

As the antiallergic active substances there are used, for example, clemastine hydrogenfumarate, chlorphenoxamine hydrochloride, dimetidine maleate, bamipine lactate or hydrochloride or other salts or esters, propylhexedrine hydrochloride tritoqualine and dephenhydramine meclozine hydrochloride.

The agents according to the present invention contain the conventional carrier material and excipients in addition to vitamin E. This fact is particularly relevant to the agents for an intended external application.

The present invention is further illustrated by the following non-limiting examples showing typical combinations of active substances and dosages.

EXAMPLE 1

100 g of an ointment contain
400 mg of allantoin;
400 mg of Dexapanthenol;
5,000 mg of D-alpha-tocopherol;
30,000 I.U. of heparin sodium.

EXAMPLE 2

100 g of an ointment contain
2.5 g of 0-(B-hydroxyethyl) rutoside;
6.5 g of D-alpha-tocopherol or D,L-alpha-tocopherol.

EXAMPLE 3

100 g of an ointment contain
400 mg of allantoin;
400 mg of Dexapanthenol;
8.8 g of D-alpha-tocopherol or D,L-alpha-tocopherol;
30,000 I.U. of heparin sodium.

EXAMPLE 4

100 g of an ointment contain
4.5 g of *Extract. Hippocastani* (contains about 800 mg of escin);
5.0 g of D-alpha-tocopherol.

EXAMPLE 5

100 g of a gel contain
50,000 I.U. of heparin sodium;
12 g of Arnica flower extract ((1:10), alcohol 60%);
25 g *Tinct. Hippocastani e sem.* (1:1, equals 0.65 g of escin);
7.5 g of D-alpha-tocopherol.

EXAMPLE 6

100 g of a gel contain
7.0 g of B-hydroxyethyl salicylate;
7.0 g of D-alpha-tocopherol.

EXAMPLE 7

100 g of an ointment contain
10 g of benzocain (anesthesin);
8 g of D-alpha-tocopherol-concentrate;
1 g of benzyl nicotinate.

EXAMPLE 8

100 g of an ointment contain
3g of B-hydroxyethyl salicylate;
1 g of benzyl nicotinate;
7 g of D-alpha-tocopherol.

EXAMPLE 9

100 g of an ointment contain
8g of D-alpha-tocopherol;
400 mg of allantoin;
400 mg of Dexapanthenol;
150,000 I.U. of heparin sodium.

EXAMPLE 10

One capsule contains
250 mg of nicotinic acid;
400 mg of D,L-alpha-tocopherol acetate;
150 mg of soybean oil.

EXAMPLE 11

One capsule contains
200 mg of B-hydroxyethyl rutoside;
300 mg of D,L-alpha-tocopherol acetate;
180 mg of soybean oil.

EXAMPLE 12

One capsule contains
150 mg of Extract. Hippocastani (contain 25 mg of escin);
300 mg of D,L-alpha-tocopherol acetate;
150 mg of soybean oil.

EXAMPLE 13

One capsule contains
300 mg of xantinol nicotinate;
400 mg of D-alpha-tocopherol;
190 mg of soybean oil.

EXAMPLE 14

One capsule contains
150 mg of Extract. Hippocastani (contain 25 mg of escin);
250 mg of vitamin E;
150 mg of soybean oil.

EXAMPLE 15

One capsule contains
5 mg of vitamin $B_1$;
5 mg of vitamin $B_2$;
5 mg of vitamin $B_6$;
200 mg of B-hydroxyethyl rutoside;
300 mg of vitamin E;
50 mg of nicotinic acid amid;
200 mg of soybean oil.

EXAMPLE 16

One capsule contains
100 mg of nicotinic acid;
100 mg of extract from horse-chestnuts (contain 16 mg of escin);
300 mg of D-alpha-tocopherol acetate;
200 mg of soybean oil.

EXAMPLE 17

One capsule contains
200 mg of inositol nicotinate;
300 mg of D-alpha-tocopherol concentrate;
150 mg of soybean oil.

EXAMPLE 18

One capsule contains
50 mg of procaine hydrochloride;
400 mg of D-alpha-tocopherol concentrate;
150 mg of soybean oil.

EXAMPLE 19

50 mg of procaine hydrochloride;
400 mg of D,L-alpha-tocopherol acetate;
5 mg of vitamin $B_1$;
5 mg of vitamin $B^2$;
5 mg of vitamin $B_6$;
150 mg of soybean oil or corn oil.

EXAMPLE 20

Drops:
100 ml of 90% Ethyl alcohol contain
40 g of D,L-alpha-tocopherol acetate;
4.5 g of *Extract. Hippocastani* (contain 750 mg of escin).

EXAMPLE 21

One capsule contains
4.5 mg of dihydroergotoxine methanesulfonate;
400 mg of D,L-alpha-tocopherol acetate.

EXAMPLE 22

One capsule contains
50 mg of procaine hydrochloride;
200 mg of nicotinic acid;
400 mg of vitamin E;
150 mg of corn oil.

EXAMPLE 23

One capsule contains
150 mg of bencyclane hydrogenfumarate;
400 mg of vitamin E as D,L-alpha-tocopherol acetate;
150 mg of soybean oil.

EXAMPLE 24

One capsule contains

| | |
|---|---|
| Pentoxifyllin | 400 mg; |
| vitamin E | 400 mg; |
| vitamin A acetate | 15,000 I.U.; |
| soybean oil | 120 mg. |

EXAMPLE 25

One capsule contains

| | |
|---|---|
| Naftidrofuryl hydrogenoxalate | 100 mg |
| vitamin E | 500 mg |
| vitamin A palmitate | 30,000 I.U. |
| soybean oil | 150 mg. |

EXAMPLE 26

One capsule contains

| | |
|---|---|
| Cinnarizine | 75 mg; |
| vitamin E | 400 mg; |
| vitamin A palmitate | 15,000 I.U.; |
| vitamins $B_1$, $B_2$, $B_6$ (in equal amounts) | 10 mg; |
| vitamin $B_{12}$ | 5 mg; |
| soybean oil | 150 mg. |

EXAMPLE 27

100 ml of drops contain in ethylalcohol

| | |
|---|---|
| Cinnarizine | 7.5 g; |
| vitamin E | 4.0 g; |
| vitamin A palmitate | 2,500,000 units. |

EXAMPLE 28

One capsule contains

| | |
|---|---|
| xantinol nicotinate | 500 mg; |
| vitamin E (D.L-alpha-tocopherol) | 400 mg; |
| vitamin A Palmitat | 10,000 I.U. |
| Tween 80 | 20 mg; |
| soybean oil | 150 mg. |

EXAMPLE 29

100 ml of drops contain in ethylalcohol dihydroerootoxine methanesulfonate 1.5 g (comprising
0.5 g of dihydroergocristine methanesulfonate,
0.5 g of dihydroergocornine methanesulfonate,
0.333 g of alpha-dihydroergocryptine methansulfonate and
0.167 g of B-dihydroergocryptine methanesulfonate);
vitamine E (D,L-alpha tocopherol acetate) 3.5 g;
vitamine A palmitate 2,500,000 units.

EXAMPLE 30

One capsule contains

| | |
|---|---|
| B-pyridyl carbinol tartrate (conforming to 150 mg of pyridylcarbinol); | 360 mg |
| D-alpha-tocopherol acetate | 400 mg; |
| vitamin A palmitate | 12,000 I.U. |
| soybean oil | 150 mg. |

EXAMPLE 31

One capsule contains

| | |
|---|---|
| DL-alpha-tocopherol | 400 mg; |
| B-hydroxyethyl rutoside | 300 mg; |
| vitamin A palmitate | 15,000 I.U. |
| soybean oil | 150 mg. |

EXAMPLE 32

One capsule contains

| | |
|---|---|
| Ginkgo flavoglycosides | 3.0 mg; |
| vitamin E DL-alpha-tocopherol acetate | 300 mg; |
| vitamin A palmitate | 25,000 I.U.; |
| soybean oil | 100 mg. |

EXAMPLE 33

One capsule contains

| | |
|---|---|
| nicotinic acid | 300 mg; |
| vitamin E | 400 mg; |
| vitamin A palmitate | 15,000 I.U.; |
| Cetiol (oleylic acid ester) | 20 mg; |
| soybean oil | 150 mg. |

EXAMPLE 34

One capsule contains

| | |
|---|---|
| DL-alpha-tocopherol acetate | 400 mg; |
| B-Hydroxyathylrutosid | 300 mg; |
| vitamin A palmitate | 25,000 I.U.; |
| soybean oil | 120 mg. |

EXAMPLE 35

One capsule contains

| | |
|---|---|
| Pentoxifylline | 400 mg; |
| vitamin E DL-alpha-tocopherol acetate | 400 mg; |
| vitamin A palmitate | 15,000 I.U.; |
| Tween 80 | 10 mg; |
| soybean oil | 150 mg. |

EXAMPLE 36

One capsule contains

| | |
|---|---|
| Bamethane sulfate | 25 mg; |
| DL-alpha-tocopherol acetate | 250 mg; |
| vitamin A palmitate | 10,000 I.U.; |
| soybean oil | 150 mg. |

EXAMPLE 37

One capsule contains

| | |
|---|---|
| Vincamine | 30 mg; |
| vitamin E DL-alpha-tocopherolacetat | 400 mg; |
| vitamin A palmitate | 30,000 I.U.; |
| soybean oil | 150 mg. |

EXAMPLE 38

100 g of an ointment contain
10 g of D-alpha-tocopherol; and
50,000 I.U. of heparin sodium;
in an ointment base comprising
22 parts of cetylstearylalcohol;
18 parts of Cetiol; and
60 parts of water.

EXAMPLE 39

100 g of an ointment contain
7 g of vitamin E (D-alpha-tocopherol);
1 g of nicotinic acid benzyl ester; and
1 g of camphor;
in ointment base comprising
17 part of cetylstearylalcohol;
8 parts of white petrolatum;
15 parts of Cetiol; and
60 parts of water (aqua conservata).

EXAMPLE 40

100 g of an ointment contain
7 g of vitamin E; and
15 g of *Tinct. calendualae;*
in an ointment base comprising
13 parts of wool wax alcohol;
2 parts of cetylstearylalcohol;
20 parts of Cetiol
5 parts of paraffin; and
50 parts of water (aqua conservata).

EXAMPLE 41

100 g of an ointment contain
8 g of vitamin E (DL-alpha-tocopherol);
1.5 g of rosemary oil;
1 g of *Extract. Hippocastani* (standardized to at least 8% of escin); and
1 g juniper oil;

ointment base as in Example 38.

EXAMPLE 42

Solution comprising
10 g of vitamin E (D-alpha-tocopherol concentrate);
1 g of dwarf pine oil (ol. pini pumilionis);
1 g of eucalyptus oil;
1 g of juniper oil;
1 g of Tween 80
ad 100 g of isopropyl alcohol.

EXAMPLE 43

100 g of an ointment contain
7 of D-alpha-tocopherol concentrate;
2 g of Tinct. arnicae;
2 g of salicylic acid B-hydroxyethyl ester;
in an ointment base as in Example 38.

EXAMPLE 44

Solution according to Example 42.
7.0 g of vitamin E;
1.0 g dwarf pine oil;
1.0 g Tinct. arnicae;
1.0 g of Cetiol
ad 100 g of isopropyl alcohol.

EXAMPLE 45

100 g of an ointment contain
9.0 g of vitamin E;
20.0 g Tinct. calendulae
in an ointment base as in Example 38.

The Examples 46 through 60 relate to combinations of the vitamins E and A with lecithin.

EXAMPLE 46

One capsule contains

| | |
|---|---|
| vitamin E (D,L-alpha-tocopherol acetate) | 400 mg; |
| vitamin A acetate | 25,000 I.U.; |
| soybean lecithin | 200 mg; |
| soybean oil | 120 mg; and |
| Tween 80 | 8 mg. |

EXAMPLE 47

One capsule contains

| | |
|---|---|
| Naftidirofuryl hydrogenoxalate | 100 mg; |
| vitamin E (D-alpha-tocopherol-concentrate) | 500 mg; |
| vitamin A palmitate | 30,000 I.U. |
| soybean lecithin | 25 mg; and |
| soybean oil | 150 mg. |

EXAMPLE 48

One capsule contains

| | |
|---|---|
| Cinnarizine | 75 mg; |
| vitamin E (D-alpha-tocopherol acetate) | 400 mg; |
| vitamin A palmitate | 25,000 I.U.; |
| vitamins B$_1$, B$_2$, B$_6$ (in equal amounts) | 10 mg; |
| vitamin B$_{12}$ | 5 mg; |
| soybean oil | 100 mg; and |
| soybean lecithin | 280 mg. |

EXAMPLE 49

100 ml of drops contain in ethyl alcohol

| | |
|---|---|
| Cinnarizine | 7.5 g; |
| vitamin E | 4.0 g; |
| vitamin A palmitate | 2,500,000 I.U. and |
| lecithin | 2.5 g. |

EXAMPLE 50

One capsule contains

| | |
|---|---|
| Xantinol nicotinate | 500 mg; |
| vitamin E (DL-alpha-tocopherol) | 400 mg |
| vitamin A palmitate | 25,000 I.U.; |
| Tween 80 | 20 mg |
| soybean oil | 150 mg; and |
| soybean lecithin | 25 mg. |

EXAMPLE 51

100 ml of drops contain in ethyl alcohol
dihydroergotoxine methanesulfonate 1.6 g (comprising
0,5 g of dihydroergocristine methanesulfonate,
0,5 g of dihydroergocornine methanesulfonate,
0,333 g of alpha-dihydroergocryptine methanesulfonate and
0,167 g of B-Dihydroergocryptine methanesulfonate);
vitamin E (DL-alpha-tocopherol acetate) 3.5 g;
vitamin A palmitate 1,500,000 I.U.; and
soybean lecithin 3.5 g.

EXAMPLE 52

One capsule contains

| | |
|---|---|
| B-pyridyl carbinol tartrate corresponds to 150 mg of pyridyl carbinol; | 360 mg |
| D-alpha-tocopherol acetate | 400 mg; |
| vitamin A palmitate | 10,000 I.U.; |
| soybean oil | 100 mg; |
| soybean lecithin | 150 mg; and |
| Tween 20 | 6 mg. |

EXAMPLE 53

One capsule contains

| | |
|---|---|
| DL-alpha-tocopherol | 400 mg; |
| B-hydroxyethyl rutoside | 300 mg; |
| vitamin A palmitate | 30,000 I.U.; |
| soybean oil | 100 mg; and |
| soybean lecithin | 250 mg. |

EXAMPLE 54

One capsule contains

| | |
|---|---|
| Ginkgo flavoglycosides | 3.0 mg |
| vitamin E (D,L-alpha-tocopherol acetate) | 300 mg |
| vitamin A palmitate | 25,000 I.U.; |
| soybean oil | 100 mg; and |
| soybean lecithin | 200 mg. |

EXAMPLE 55

One capsule contains

| | |
|---|---|
| nicotinic acid | 300 mg; |
| vitamin E | 400 mg; |
| vitamin A palmitate | 15,000 I.U.; |
| Cetiol (Oleic acid ester) | 10 mg; |
| soybean oil | 100 mg; and |
| soybean lecithin | 20 mg. |

EXAMPLE 56

One capsule contains

| | |
|---|---|
| D-alpha-tocopherol | 200 mg; |
| lecithin | 500 mg; |
| soybean oil | 180 mg; and |
| Tween 80 | 10 mg. |

EXAMPLE 57

Capsules in accordance with Example 56, but additionally containing 15,000 I.U. vitamin A palmitate.

EXAMPLE 58

Capsules in accordance with Examples 56 and 57, but containing D,L-alpha-tocopherol acetate instead of D-alpha-tocopherol.

EXAMPLE 59

One capsule contains

| | |
|---|---|
| D-alpha-tocopherol | 400 mg; |
| lecithin | 400 mg; |
| soybean oil | 200 mg; and |
| Tween 80 | 15 mg. |

EXAMPLE 60

Capsules in accordance with Example 59, but additionally containing 15,000 I.U. vitamin A palmitate or vitamin A acetate or 9,5 mg B-carotene.

The products according to the Examples 46 through 60 can be used as agents for lowering the cholesterol level.

The following examples relate to vitamin E preparations which additionally contain dimethylaminoethanol.

EXAMPLE 61

One capsule contains
20 mg of dimethylaminoethanol;
400 mg of D,L-alpha-tocopherol acetate;
50 mg of soybean oil;
200 mg of soybean lecithin; and
200 mg of B-hydroxyethylrutoside.

EXAMPLE 62

One capsule contains
20 mg of dimethylaminoethanol;
400 mg of D,L-alpha-tocopherol acetate;
12,000 I.U. of vitamin A palmitate (6,67 mg);
100 mg of soybean oil;
300 mg of lecithin;
8 mg of Tween 80; and
75 mg of Cinnarizine.

EXAMPLE 63

One capsule contains
25mg of dimethylaminoethanol orotate;
400 mg of D,L-alpha-tocopherol acetate;
15,000 I.U. of vitamin A palmitate (8.33 mg);
20 mg of soybean lecithin: and
400 mg nicotinic acid.

EXAMPLE 64

As Example 61, but with use of 8 mg of Tween 80.

EXAMPLE 65

One capsule contains
25 mg of dimethylaminoethanol orotate;
500 mg of D-alpha-tocopherol concentrate;
22,000 I.U. of vitamin A palmitate (12,22 mg);
28 mg of soybean lecithin;
120 mg of soybean oil; and
3.0 mg of Ginkgoflavoglucoside.

EXAMPLE 66

Combination according to Example 65, but with use of 8 mg of Tween 20.

EXAMPLE 67

One capsule contains
30 mg of dimethylaminoethanol orotate;
400 mg of D,L-alpha-tocopherol acetate;
300 mg of lecithin;
8 mg of Tween 80; and
30 mg of Vincamine.

EXAMPLE 68

One capsule contains
25 mg of dimethylaminoethanol orotate;
350 mg of D-alpha-tocopherol acetate;
15,000 I.U. of vitamin A palmitate;
5 mg of each of the vitamins $B_1$, $B_2$, $B_6$;
5 mg of vitamin $B_{12}$;
15 mg of nicotinic acid amide;
280 mg of lecithin; and
75 mg Cinnarizine.

EXAMPLE 69

Combination according to Example 68, but with use of 5 mg of Tween 80.

EXAMPLE 70

One capsule contains
25 mg of dimethylaminoethanol orotate;
400 mg of D,L-alpha-tocopherol acetate;
15,000 I.U. of vitamin A palmitate *8,33 mg); and
300 mg of B-hydroxyethylrutoside.

EXAMPLE 71

Combination according to Example 70, but with use of 8 mg of Tween 80.

EXAMPLE 72

One capsule contains
35 mg dimethylaminoethanol orotate;
500 mg of D-alpha-tocopherol concentrate;
22,000 I.U. of vitamin A palmitate (12,22 mg); and
400 mg of xantinol nicotinate.

EXAMPLE 73

Combination according to Example 72, but with use of 4 mg of Tween 20.

EXAMPLE 74

One capsule contains 30 mg of dimethylaminoethanol orotate;
400 mg of D,L-alpha-tocopherol acetate; and
400 mg of Pentoxyfylline.

EXAMPLE 75

One capsule contains
35 mg of dimethylaminoethanol orotate;
350 mg of D-alpha-tocopherol acetate;
15,000 I.U. of vitamin A palmitate;
5 mg of each of the vitamins $B_1$, $B_2$ and $B_6$;
5 mg of vitamin $B_{12}$; and
100 mg of Bencyclane fumarate.

EXAMPLE 76

Combination according to Example 75, but with use of 3 mg of Tween 80.

EXAMPLE 77

One capsule contains
25 mg of dimethylaminoethanol orotate;
350 mg of D,L-alpha-tocopherol acetate; 17,000 I.U. (9,44 mg) of vitamin A palmitate;
70 mg of soybean oil; and
75 mg Cinnarizine.

EXAMPLE 78

One capsule contains
20 mg of dimethylaminoethanol;
200 mg of D,L-alpha-tocopherol acetate;
12,000 I.U. of vitamin A palmitate (6,67 mg);
50 mg of soybean oil; and
250 mg of soybean lecithin.

EXAMPLE 79

One capsule contains
35 mg of dimethylaminoethanol orotate;
400 mg of D,L-alpha-tocopherol acetate;
15,000 I.U. of vitamin A palmitate (8,33 mg); and
20 mg of soybean lecithin.

EXAMPLE 80

Combination according to Example 78, but with use of 3 mg of Tween 80.

EXAMPLE 81

One capsule contains
20 mg of dimethylaminoethanol;
200 mg of D,L-alpha-tocopherol acetate;
12,000 I.U. of vitamin A palmitate (6,67 mg); and
50 mg of soybean oil.

EXAMPLE 82

One capsule contains
35 mg of dimethylaminoethanol orotate;
400 mg of D,L-alpha-tocopherol acetate; and
15,000 I.U. of vitamin A palmitate (8,33 mg).

EXAMPLE 83

Combination according to Example 81, but with use of 3 mg of Tween 80.

EXAMPLE 84

One capsule contains
35 mg of dimethylaminoethanol orotate;
500 mg of D-alpha-tocopherol concentrate: and
22,000 I.U. of vitamin A palmitate (12,22 mg).

EXAMPLE 85

Combination according to Example 84, but with use of 4 mg of Tween 20.

EXAMPLE 86

One capsule contains
30 mg of dimethylaminoethanol orotate; and
400 mg of D,L-alpha-tocopherol acetate;

EXAMPLE 87

One capsule contains
35 mg of dimethylaminoethanol orotate;
350 mg of D-alpha-tocopherol acetate;
15,000 I.U. of vitamin A palmitate;
5 mg of each of the vitamins $B_1$, $B_2$ and $B_6$;
5 mg of vitamin $B_{12}$; and
15 mg of nicotinic acid amide.

EXAMPLE 88

Combination according to Example 93, but with use of 3 mg of Tween 80.

EXAMPLE 89

One capsule contains
25 mg of dimethylaminoethanol orotate;
350 mg of D,L-alpha-tocopherol acetate;
17,000 I.U. (9,44 mg) of vitamin A palmitate; and
70 mg of soybean oil.

In all of the Examples there was used soybean oil in an amount of from 50 to 200 mg per capsule. However, other neutral oils such as olive oil, rape seed oil etc. can be used as well.

EXAMPLE 90

A solution for external application, more specifically as a spray, contains
33 parts of D-alpha-tocopherol concentrate:
8 parts of phosphorlipids;
99 parts of isopropyl alcohol;
45 parts of isopropyl alcohol (70%).

EXAMPLE 91

One capsule contains
600 mg D-alpha-tocopherol concentrate;
5,000 I.U. of vitamin A;
8 mg of Tween 80; and
120 mg of soybean oil.

EXAMPLE 92

One capsule contains
400 mg of D-alpha-tocopherol;
8.250 mg of vitamin A; and
8 mg of Tween 80.

EXAMPLE 93

One capsule contains
500 mg of D,L-alpha-tocopherol acetate;
100 mg of soybean oil;
1,000 mg of D,L-alpha-tocopherol acetate;
10 mg of Tween 80; and
150 mg of soybean oil.

EXAMPLE 94

One capsule contains
30 mg of chlorphenoxamine hydrochloride;
400 mg of D,L-alpha-tocopherol acetate;
50 mg of nicotinic acid; and 100 mg of soybean oil.

EXAMPLE 95

In accordance with Example 94, but 40 mg of chlorphenoxamine hydrochloride are used instead of 30 mg, and 20,000 I.U. of vitamin A palmitate are added.

EXAMPLE 96

One capsule contains
70 mg of Bamipine hydrochloride;
500 mg of D-alpha-tocopherol concentrate;
100 mg of Troxerutin; and
80 mg of peanut oil.

EXAMPLE 97

One capsule contains
120 mg of tritoqualine;
300 mg of D-alpha-tocopherol acetate;
100 mg of troxerutin; and
80 mg of soybean oil.

EXAMPLE 98

100 g of an ointment contain
40.0 g of clemastine hydrogenfumarate;
8.0 g of D-alpha-tocopherol concentrate; and
60,000 I.U. of heparin sodium;
in an ointment base comprising
20.0 parts of Cetiol (oleic acid oleylester);
20.0 parts of cetylstearylalcohol; and
60.0 parts of *aqua conservata*.

EXAMPLE 99

100 g of an ointment contain
1.5 g of chlorphenoxamine hydrochloride;
10 g of D,L-alpha-tocopherol; and
50,000 I.U. of heparin sodium;
in an ointment base as in Example 98.

EXAMPLE 100

One capsule contains
70 mg of bamipine hydrochloride;
400 mg of D-alpha-tocopherol concentrate; and
30 mg of cinnarizine.

EXAMPLE 101

According to Example 98, however including 3% of Calendulae oil.

EXAMPLE 102

100 g of an ointment contain
5 g of D-alpha-tocopherol concentrate;
10.000 I.U. of vitamin A palmitate;
50.000 I.U. of heparin sodium; and
in Eucerin anhydricum.

EXAMPLE 103

Same as in Example 102, however containing 8 g of D-alpha-tocopherol concentrate.

The following combinations are ointments containing Bufexamac for the treatment of skin inflammations.

EXAMPLE 104

100 g of an ointment contain
5.0 g of Bufexamac; and
8.0 g of D-alpha-tocopherol concentrate;
in an ointment base consisting of
20% of cetylstearylalcohol;
20% of Cetiol (oleic acid oleylester); and
60% *aqua conservata*.

EXAMPLE 105

100 g of an ointment contain
5.0 g Bufexamac; and
8.0 g of D,L-alpha-tocopherol in an ointment base as in Example 104, however containing 55% of water and 5% of white petrolatum instead of 60% of water.

EXAMPLE 106

100 g of an ointment contain
10.0 g of D-alpha-tocopherol;
500 mg of dexapanthenol; and
300 mg of allantoin
in an ointment base as in Example 104.

EXAMPLE 107

100 g of an ointment contain
4.0 g of Bufexamac;
8.0 g of D-alpha-tocopherol;
400 mg of dexapanthenol; and
400 mg of allantoin
in an ointment base as in Example 104.

EXAMPLE 108

Ointment as in Example 107, however *Ungt. Cordes* was used as the ointment base.

EXAMPLE 109

Ointment as in Example 106, however triglyceride mixtures were used as the ointment base.

The following Examples relate to vitamin E preparations containing antiallergic agents.

EXAMPLE 110

One capsule contains
30 mg of chlorphenoxamine hydrochloride;
400 mg of D,L-alpha-tocopherol acetate; and
100 mg of soybean oil.

EXAMPLE 111

In accordance with Example 110, however using 40 mg of chlorphenoxamine hydrochloride instead of 30 mg and in addition thereto 20,000 I.U. of vitamin A palmitate.

EXAMPLE 112

One capsule contains
70 mg of bamipine hydrochloride;
500 mg of D-alpha-tocopherol concentrate; and
80 mg of peanut oil.

EXAMPLE 113

One capsule contains
120 mg of tritoqualine;
300 mg of D-alpha-tocopherol acetate; and
80 mg of soybean oil.

EXAMPLE 114

100 g of an ointment contain
40.0 g of clemastine hydrogenfumarate; and
8.0 g of D-alpha-tocopherol concentrate;
in an ointment base comprising
20.0 parts of Cetiol (oleic acid oleylester);
20.0 parts of cetylstearylalkohol; and
60.0 parts of *aqua conservata*.

EXAMPLE 115

100 g of an ointment contain
1.5 g of chlorphenoxamine hydrochloride; and
10 g of D,L-alpha-tocopherol
in an ointment base as in Example 114.

The following Examples relate to light-protective agents.

EXAMPLE 116

100 g of an ointment contain
8 g of D-alpha-tocopherol concentrate;
2 g of phospholipids; and
2 g of 4-phenylbenzophenone-2-carboxylic acid isooctylester
in an ointment base comprising
22 parts of cetylstearylalcohol;
18 parts of Cetiol (oleic acid oleylester); and
60 parts of water.

EXAMPLE 117

100 g of an ointment contain
3 g of hydroxyethyl salicylate;
1 g of benzyl nicotinate;
8 g of D-alpha-tocopherol concentrate; and
2 g of phospholipids
in an ointment base as in Example 116.

EXAMPLE 118

100 g of an ointment contain
50.000 I.U. of heparin sodium;
12.0 g of Arnica Lebuten extract 1 =10 (alkal 60%);
7.5 g of D-alpha-tocopherol concentrate;
3 g of phospholipids;
0.5 g of linoleic acid; and
0.15 g of linolenic acid
in an ointment base as in Example 116.

EXAMPLE 119

100 g of an ointment contain
1.5 g of chlorphenoxamine hydrochlorid;
8 g of D-alpha-tocopherol concentrate; and
2 g of phospholipids in an ointment base as in Example 116.

EXAMPLE 120

100 g of an ointment contain
10.0 g of D-alpha-tocopherol concentrate;
2.0 g of benzarone; and
2 g of phospholipids
in an ointment base as in Example 116.

EXAMPLE 121

100 g of a cream contain
10 g of D-alpha-tocopherol concentrate; and
2 g Eusolex ® (8020 Merck)
in an ointment base comprising
22 parts of cetylstearylalcohol;
18 parts Cetiol; and
60 parts of water (*aqua conservata*).

EXAMPLE 122

100 g of a cream contain
8 g of D,L-alpha-tocopherol concentrate; and
3 g of Eusolex ® (232 Merck);
in an ointment base as in Example 121.

EXAMPLE 123

100 g of a cream contain
12 g of vitamin E; and
1 g Eusolex ® (8020 Merck);
in an ointment base as in Example 121.

EXAMPLE 124

100 g of a cream contain
9.0 g of vitamin E; and
0.3 g Eusolex ® (8020 Merck);
in an ointment base comprising
17 parts of cetylstearylalcohol;
8 parts of white petrolatum;
15 parts Cetiol; and
60 parts of water (aqua conservata).

EXAMPLE 125

100 g of an ointment contain
8.00 g of vitamin E;
2.00 g of phospholipids;
0.50 g of linolenic acid; and
0.15 g of linolenic acid;
in an ointment base as in Example 121.

EXAMPLE 126

Ointment according to Example 121, however including 1.0 g of Eusolex ® (8020 Merck) per 100 g.

EXAMPLE 127

100 g of an ointment contain
15 g of vitamin E
in an ointment base as in Example 121.

EXAMPLE 128

One capsule contains
35 mg of xanthaxanthin;
8 mg of B-carotene:
8 mg of calcium D-Pantothenate;
0.15 mg of D-biotin;
250 mg of lecithin;
400 mg of D,L-alpha-tocopherol acetate; and
80 mg of soybean oil.

EXAMPLE 129

One capsule contains
30 mg of xanthaxanthin
300 mg of D-alpha-tocopherol concentrate; and
150 mg of soybean oil.

EXAMPLE 130

One capsule contains
15 mg of B-carotene;
400 mg of D-alpha-tocopherol acetate; and
120 mg of soybean oil.

EXAMPLES 131 to 137 and COMPARATIVE EXAMPLE

Eight light-protective agents as set forth hereinbelow were tested with human volunteers for determining the erythema-preventing activity.

EXAMPLE 131

"Vitamin E Natur"
containing 8% by weight of D-alpha-tocopherol.

EXAMPLE 132

"DL Hep Na"

containing 8% by weight of D,L-alpha-tocopherol and 50,000 I.U. of heparin sodium.

EXAMPLE 133

"Vitamin E COO/8 55,000 Hepa Na"
containing 8% by weight of natural vitamin E and 55.000 I.U. of heparin sodium

EXAMPLE 134

"Vitamin E +COO BN 8/1.5"
containing 8% by weight of natural vitamin E and 1.5% by weight of benzyl nicotinate.

EXAMPLE 135

"8 Gew.-% Covitol und 4 Gew.-% Arnika"
containing 8% by weight of natural vitamin E and 2% by weight of Arnica oil.

EXAMPLE 136

"8 Gew.-% Covitol
2 Gew.-% Campher
2 Gew.-% Menthol
10 Gew.-% Pfefferminzol
70 Gew.-% Lanette"
containing 8% by weight of natural vitamin E and the other aforementioned ingredients.

EXAMPLE 137

"8 Gew.-% Covitol
10 Gew.-% Calendulae oil
74 Gew.-% Lanette"
containing 8% by weight of natural vitamin E.

COMPARATIVE EXAMPLE "Unguentum Lanette DHW Art. 226/15270"

All products, except for the Lanette ointment, were white ointment-like emulsions.

The products met the requirements as set forth for such cosmetics. They could be readily and uniformly applied to the skin and did not create any layer thereon that would have any striking features of gloss, tackiness or oiliness.

During the applications none of the test persons reported any missensations such as itch, burn or tension of the skin or any excessive feeling of cold or heat.

Upon the examination of the skin 24 hours after the application there were, outside the erythema reactions, no skin changes that would have indicated any (photo)-toxic or (photo)allergic effects caused by the products.

Test Method:

The light-protective activity was determined as the average protective factor according to SCHULZE with 20 test persons of different ages, sexes and skin types who had healthy skin. Unless explicitly otherwise stated, the method used was that in accordance with DIN-Norm 67 501. The product was uniformly applied in an amount of 150 mg/100 cm$^2$ on the skin.

Exposure to light was effected as usual by employing four lamps Osram ®-Ultravitalux-Lampen at a distance of 30 cm from each other and from the back of the test person. The erythema threshold period of time was recorded after about 24 hours. The individual protection factor is the quotient of the erythema threshold period of the protected skin and the erythema threshold period of the unprotected skin. Any intermediate values (e.g. 1.7; 3.4 etc.) result from the fact that the two control areas adjacent to the test area show different erythema threshold periods or the test area allows a lower increase in intensity than that of the control areas to be recorded.

RESULTS:

In the test as thus carried out with the 20 test persons of different ages, sexes and skin types the average protection factors (underscored) as set forth hereinafter were found as the arithmetic means from the individually measured values (given in brackets):

EXAMPLE 131

3.28 (5×2.0; 5×2.8; 9×4.0; 1×5.6).

EXAMPLE 132

4.38 (1×2.0; 2×2.8; 11×4.0; 5×5.6; 1×8.0).

EXAMPLE 133

4.02 (2×2.0; 9×2.8; 6×4.0; 2×8.0; 1×11.2).

EXAMPLE 134

4.21 (1×1.4; 5×2.0; 4×2.8; 3×4.0; 4×5.6; 2×8.0; 1×11.2)

EXAMPLE 135

2.72 (4×1.4; 3×2.0; 9×2.8; 3×4.0; 1×5.6).

EXAMPLE 136

2.88 (6×2.0; 10×2.8; 3×4.0; 1×5.6).

EXAMPLE 137

3.94 (2×2.0; 5×2.8; 9×4.0; 3×5.6; 1×8.0).

COMPARATIVE EXAMPLE

Lanette ointment:
1.07 (1×0.7; 15×1.0; 4×1.4).

A commercially available preparation (Standard Preparation K 17 N), which previously had shown an average protection factor of 3.82 in a test with 220 test persons yielded an arithmetic mean value 3.74 in the present test.

Due to the above data and upon comparing same with the results obtained with numerous test products and commercially available products under the same conditions and in practice, the products of the Examples 131, 135 and 136 are to be rated as nearly medium-active light-protective agents and the other products as medium-active to strongly active light-protective agents.

While the base material, Unguentum lanette, does not have any light-protective properties as expected, the other seven products may be divided into two groups due to their different properties; the differences in part being statistically significant.

One group displays a relatively weak activity and contains either exclusively the natural vitamin (product of Example 131) or, in addition to 8% by weight of vitamin E, various additives (product of Example 136) or Arnica oil (product of Example 135).

In contrast hereto there is the other group the members of which are much more active. They either contain heparin, as the products of Examples 132 and 133 do, or they contain 1.5% by weight of benzyl nicotinate (product of Example 134) or 10% by weight Calendulae oil (product of Example 137).

These results allow several conclusions to be drawn: First it is to be stated that vitamin E in its natural form as well as in its racemic form has a distinct light-protective activity, which apparently can still be enhanced, more specifically by the addition of heparin. A similar effect is also brought about by the addition of relatively high amounts of Calendulae oil and, surprisingly, the hyperemizing benzyl nicotinate as well

What is claimed is:

1. A pharmaceutical composition effective for treatment of skin conditions of allergy, tetter, inflammation, itch, wrinkles and damage from wounds, and for protection of skin from ultraviolet light, comprising at least 200 mg vitamin E per dosage unit and at least one component selected from the group consisting of a blood circulation-promoting agent and a vasodilator, said composition being admixed with a suitable pharmaceutical vehicle.

2. The composition according to claim 1, wherein said blood circulation promotor is selected from the group consisting of nicotinic acid benzyl ester, pure arnica oil, calendula oil, heparin sodium, $\beta$-Hydroxyethylrutoside, dihydroergotoxine methanesulfonate, dihydroergocristine methanesulphonate, $\beta$-hydroxyethylsalic 01. juiperi, 01. pini pumilionis, 01. eucalypti, 01. rosmarinae, Tinct. camphorae, Pentoxifylline or Bencyclan hydrogenfumarate.

3. The composition according to claim 1 further containing at least one ingredient selected from the group consisting of vitamin C, vitamin A, a vitamin of the B series, at least one unsaturated fatty acid, silicone oil, polysiloxane, an emulsifie:, beta-carotene, and an amino acid.

4. The composition according to claim 3, wherein said emulsifier is lecithin.

5. The composition according to claim 3, wherein said unsaturated fatty acid comprises one or more components selected from the group consisting of linoleic acid, linolenic acid, and oleic acid.

6. The composition according to claim 3, wherein said composition contains from 5,000 to 25,000 International Units of vitamin A per dosage unit.

7. The composition according to claim 1, further containing ultra-violet light stabilizers.

8. The composition according to claim 7, further containing antihistaminics.

9. The composition according to claim 1, wherein said composition further contains up to 12% by weight of Bufexamac, based on the weight of the composition.

10. The composition according to claim 9, wherein said composition contains from 3 to 10% by weight of Bufexamac, based on the weight of the composition.

11. The composition according to claim 1, wherein said composition is formulated as a capsule.

12. The composition according to claim 11, wherein said composition contains for 200 mg to 1,000 mg of vitamin E per dosage unit.

13. The composition according to claim 12, wherein said composition contains form 250 mg to 600 mg of vitamin E per dosage unit.

14. The composition according to claim 13, wherein said composition contains for 300 mg to 500 mg of vitamin E per dosage unit.

15. The composition according to claim 14, wherein said composition contains from 6,000 to 15,000 I.U. of vitamin A per dosage unit.

16. The composition according to claim 1, wherein said composition is formulated for topical application as a cream, gel, ointment, milk, lotion or solution.

17. The composition according to claim 16, wherein said composition contains from 0.5 to 20% by weight of vitamin E, based on the weight of the composition.

18. The composition according to claim 17, wherein said composition contains from 4 to 10% by weight of vitamin E, based on the weight of composition.

19. The composition according to claim 1, wherein said composition is formulated as spray, tincture or solution in an alcoholic solvent for topical application.

20. The composition according to claim 19 wherein said solvent is isopropyl alcohol.

21. The composition according to claim 19, wherein said composition contains up to 32% by weight of vitamin E, based on the weight of the composition.

22. The composition according to claim 19, wherein said composition contains up to 25% by weight of vitamin E, based on the weight of the composition.

23. The composition according to claim 16, further containing one or more ingredients selected from the group consisting of lecithin and amino acids.

24. An ointment for topical administration effective for treatment of skin conditions of allergy, tetter, inflammation, itch, wrinkles and damage from wounds, and for protection of skin from ultra-violet light, comprising from 0.5 to 20% by weight of vitmanin E, based on the weight of the composition, and at least one component selected from the group consisting of a blood circulation-promoting agent and a vasodilator, said composition being admixed with a suitable pharmaceutical vehicle.

25. The ointment according to claim 24, wherein said blood circulation promoter is selected from the group consisting of nicotinic acid benzyl ester, pure arnica oil, calendula oil hepario sodium $\beta$-Hydroxyethylrutoside, dihydroergotoxine methanesulfonate, dihydroergocristine methanesulphonate, $\beta$-hydroxyethylsalicylate, 01. juniperi, 01. pini pumilionis, 01.eucalypti, 01. rosmarinae, Tinct camphorae, Pentoxifylline or Bencyclan hydrogenfumarate.

26. The ointment according to claim 24, further containing at least one ingredient selected from the group consisting of vitamin C. vitamin A, a vitamin of the B series at least one unsaturated fatty acid, a silicone oil, polysiloxane, an emulsifier, beta-carotene, and an amino acid.

27. The ointment according to claim 26, wherein said emulsifier is lecithin.

28. The ointment according to claim 26, further containing ultra violet light stabilizers.

29. The ointment according to claim 26, wherein said unsaturated fatty acid comprises one or more components selected from the group consisting of linoleic acid, linolenic acid and oleic acid.

30. The ointment according to claim 24, wherein said ointment contains from 4 to 10% by weight of vitamio E, based on the weight of the composition.

31. The ointment according to claim 24, wherein said ointment contains up to 32% by weight of vitamin E, based on the weight of the composition.

32. A method of treating skin conditions in a mammal including tetter, inflammation, itch, wrinkles, damage from wounds or exposure to ultra-violet light, comprising the adminstration of an effective dose of a pharmaceutical composition comprising at least 200 mg vitamin E and at least one component selected from the group consisting of a blood circulation-promoting agent an a vasodilator.

33. The method of claim 32, wherein said composition further contains up to 12% by weight of Bufexamac, based on the weight of the composition.

34. The method of claim 33, wherein said composition contains from 3 to 10% by weight of Bufexamac based on the weight of the composition.

35. The method of claim 32, wherein said composition further contains one or more ultra-violet light stabilizers.

36. The method of claim 35, wherein said pharaceutical composition further contains antihistamines.

37. The method of claim 32, wherein said blood circulation promoter is selected from the group consisting of nicotinic acid benzyl ester, pure arnica oil, calaendula oil, heparin sodium β-Hydroxyethylrutoside, dihydroergocristine methanesulfonate, dihydroergocristine methanesulphonate, β-hydroxyethylsalicylate, 01. *juniperi*, 01. *pini pumilionis*, 01. *eucalypti*, 01. *rosmarinae*, Trinct. *camphorae*, Pentoxifylline or Bencyclan hydrogenfumarate.

38. The method of claim 32, wherein said pharmaceutical composition is administered orally.

39. The method of claim 33, wherein said composition is administered in the form of capsules.

40. The method of claim 39, wherein each of said capsules contains from 200 to 1,000 mg of vitamin E.

41. The method claim 40, wherein each of said capsules contains from 250 to 600 mg of vitamin E.

42. The method of claim 41, wherein each of said capsules contains from 300 to 500 mg of vitamin E.

43. The method of claim 32, wherein said pharmaceutical composition is administered topically.

44. The method of claim 43, wherein said composition is administered in the form of a cream, gel, ointment, milk, lotion, or solution.

45. The method of claim 44, wherein said composition contains from 0.5 to 20% by weight of vitamin E, based on the weight of the composition.

46. The method of claim 45, wherein said composition contains from 4 to 10% by weight of vitamin E, based on the weight of the composition.

47. The method of claim 43, wherein said composition is administered in the form of a spray, tincture or solution in an alcoholic solvent.

48. The method of claim 47, wherein said alcoholic solvent is isopropyl alcohol

49. The method of claim 48, wherein said composition contains up to 25% by weight of vitamin E, based on the weight of the composition.

* * * * *